US006576254B1

(12) United States Patent
Uchegbu

(10) Patent No.: US 6,576,254 B1
(45) Date of Patent: Jun. 10, 2003

(54) POLYAMINO ACID VESICLES

(75) Inventor: Ijeoma Florence Uchegbu, Glasgow (GB)

(73) Assignee: University of Strathclyde, Glasgow (GB)

( * ) Notice: Subject to any disclaimer, the term of this patent is extended or adjusted under 35 U.S.C. 154(b) by 0 days.

(21) Appl. No.: 09/700,932

(22) PCT Filed: May 24, 1999

(86) PCT No.: PCT/GB99/01627

§ 371 (c)(1),
(2), (4) Date: Dec. 13, 2000

(87) PCT Pub. No.: WO99/61512

PCT Pub. Date: Dec. 2, 1999

(30) Foreign Application Priority Data

May 23, 1998 (GB) .............................. 9811059

(51) Int. Cl.[7] .......................... A61K 9/127; C08G 69/48
(52) U.S. Cl. .................... 424/450; 424/193.1; 424/486; 514/2; 514/44; 514/772.1
(58) Field of Search .................... 424/193.1, 196.11, 424/199.1, 202.1, 204.1, 450, 486; 514/2, 44, 772.1, 937, 938, 939, 941, 943; 525/54.1, 540, 927

(56) References Cited

U.S. PATENT DOCUMENTS

| 5,534,241 A | * | 7/1996 | Torchilin et al. | ........ 424/9.321 |
| 5,534,259 A | * | 7/1996 | Zalipsky et al. | ............ 424/450 |
| 5,889,153 A | * | 3/1999 | Suzuki et al. | ................ 530/350 |
| 5,965,404 A | * | 10/1999 | Buschle et al. | .......... 435/69.52 |
| 6,114,388 A | * | 9/2000 | Geffard | ........................ 514/563 |
| 2002/0082198 A1 | * | 6/2002 | Sakurai et al. | .................. 514/2 |

FOREIGN PATENT DOCUMENTS

| EP | 0 481 526 A | 4/1992 |
| FR | 2 574 185 A | 6/1986 |
| WO | 96/04001 A1 | * 2/1996 |
| WO | 97/04744 A1 | * 2/1997 |

OTHER PUBLICATIONS

Zhou et al. Lipophilic polylysines mediate efficient DNA transfection in mammalian cells. Biochim. Biophys. Acta. 1997, vol. 1065, pp. 8–14.*

King et al. Preparation Of Protein Conjugates With Alkoxy-polyethylene Glycols. Int. J. Peptide Protein Res. 1980. vol. 16, pp. 147–155.*

Uchegbu et al. Polymeric Vesicles From Amino Acid Homopolymers. Proceed Int'l. Symp. Control. Rel. Bioact. Mater. 1998, vol. 25, pp. 186–187.*

Uchegbu, I.F., Florence, A.T., Non–Ionic Surfactant Vesicles (Niosomes): Physical and Pharmaceutical Chemistry, Adv. Coll. Interf. Sci., (1995), pp. 1–55, vol. 58.

Lasic, Danilo, Synthetic lipid microspheres serve as multi purpose vesicles for delivery of drugs, genetic material and cosmetics, Amer. Sci., (1992) pp. 20–31, vol. 80.

P. Dash et al, "Synthetic polymers for vectorial delivery of DNA", Journal Of Controlled Release, vol. 48, 1997, pp. 269–276.

* cited by examiner

*Primary Examiner*—Jeffrey E. Russel
(74) *Attorney, Agent, or Firm*—Alston & Bird LLP

(57) ABSTRACT

There is provided polymeric vesicles formed from polyamino acid derivatives for use in the delivery of therapeutic agents. The polyamino acid is modified so as to bear at least one hydrophilic group and at least one hydrophobic group. Vesicle formation is then induced in the presence of cholesterol. The vesicles are suited for entrapment or conjugation of pharmaceutically active agents, in particular nucleic acids.

23 Claims, 4 Drawing Sheets

POLYAMINO ACID VESICLES

The present invention relates to polymeric vesicles formed from polyamino acid derivatives. The polyamino acid is modified so as to bear at least one hydrophilic group and at least one hydrophobic group. Vesicle formation is then induced in the presence of cholesterol. The vesicles are suited for entrapment or conjugation of pharmaceutically active agents, in particular nucleic acids.

The understanding of the human genome has led to a profound appreciation of the genetic basis of diseases such as cancer. The refractory nature of many solid cancers to conventional treatments coupled with the significant ageing of Western population means that fatalities associated with these cancers are likely to rise. Increasingly alternative modes of treatment are being sought, one of which is the use of deoxyribonucleic acid (DNA) as a therapeutic agent. The use of medicinal genes (gene therapy) is exemplified by the administration of prodrugs that are activated by a gene product. The targeting of this gene to tumours will localise therapy to specific areas.

Additionally, the use of gene medicines prophylactically to either add tumour suppressor genes or obscure pathogenic mutations by gene replacement has been advocated. The engineering of the expression of a gene product that stimulates the immune system to destroy cancer cells is another area awaiting exploitation.

Apart from the treatment of solid tumours other incurable genetic diseases such as cystic fibrosis and sickle cell anaemia that typically kill their victims before they reach reproductive age are also likely to benefit from treatment with gene medicines. Cystic fibrosis has received a great deal of attention recently as not only viral but non-viral gene delivery systems have been used experimentally against this disease in the clinic and although gene expression was detected with the use or a non-viral gene medicine, this expression was transient in nature.

Advances in recombinant DNA technology have meant that the development of the active ingredient in gene medicines i.e. the gene itself is now possible. However the delivery of genetic material to the sites of pathology still remains a major hurdle.

Viral gene delivery vectors have been tested and found to give stable expression in the case of adenoviruses. However, adenoviruses precipitate a severe immunological reaction that precludes administration of a repeat dose of the gene.

Retroviruses on the other hand which hold the advantage of preferentially infecting actively dividing cells are more likely to insert DNA in the host genome with unknown consequences.

Non viral gene delivery systems fall in to two broad classes: cationic polymeric systems, incorporating targeting ligands which form a transfection competent ionic complex with the gene of interest and self-assembled cationic amphiphiles—cationic liposomes which form a transfection competent complex between the amphiphilic components of the liposomes and the gene. These systems are found to transfect cells well in culture but in vivo gene expression is very low and of a transient nature.

Polylysine has previously been modified by the attachment of phospholipid groups and used in DNA transfection (Zhou, X H et al (1991) Biochim. Biophys. Acta 1065: 8–14 and Zhou, X h, Huang L (1994) Biochim. Biophys Acta 1189: 195–203).

Polylysine has also been modified by the attachment of hydrophilic groups such as polyethylene glycol (Azinger H, et al 1981) Makromol Chemie-Rapid Commum. 2: 637–640 and Dash P R, et al (1997) J. Contr. Rel. 48: 269–276) and various sugars (Kollen W J W, et al, (1996) Human Gene Ther. 13: 1577–1586 and Erbacher P, et al (1997) Biochimica Biophysica Acta 1324: 27–36).

In addition various drugs (Hudecz F. et al (1993) Bioconjugate chemistry 4: 25–33) and targeting residues such as transferrin (Wagner, E (1994) Adv. Drug Delivery Rev. 14: 113–135), asialoglycoprotein (Chowdhury, N R et al (1993) J. Biol. Chem. 268: 11265–11271) and monoclonal antibodies (Chen, J B et al (1994) Febs Lett 338: 167–169) have been conjugated to polylysine.

FR2574185 relates to lysine polymers intended for use as supports for the preparation of reagents for the diagnosis of haptenic allergies wherein the molecules have the same number of L-lysine radicals between 8 and 20 and have been modified so as to include alternating hydrophilic and hydrophobic substituents.

According to the present invention there is provided a compound which is a derivatised polyamino acid bearing at least one hydrophilic group and at least one hydrophobic group per molecule.

The polyamino acid is preferably a straight chain homo- or heteropolymer joined by amide linkages and may be of natural or synthetic origin. Most preferably the polyamino acid is a straight chain homopolymer. Preferred straight chain homopolymers include poly-L-lysine and poly-L-ornithine, or any other amide linked heteropolymer made from amino acids. The polyamino acid may have a molecular weight of about 600–1,000,000, preferably 15,000–30,000.

Preferably the hydrophilic group is cationic or non-ionic. In one embodiment, DNA is designed to be associated with the compound when assembled as a vesicle. An anionic hydrophilic group would however repel anionic DNA. The hydrophilic group may be selected from hydrophilic drug molecules or ligands, sugars, oligosaccharides, polyhydroxy molecules e.g. sorbitol or various organic groups.

Typical organic groups nay be selected from mono- and oligo-hydroxy $C_{1-6}$ alkyl, mono- and oligo-hydroxy substituted $C_{2-6}$ acyl, $C_{1-2}$ alkoxy alkyl optionally having one or more hydroxy groups substituted on the alkoxy or alkylene groups, oligo- or poly-(oxa $C_{1-3}$ alkylene) preferably polyoxyethylene comprising up to about 120 ethylene oxide units (i.e. up to a molecular weight of 5000), and $C_{1-4}$ alkyl (oligo- or poly-oxa $C_{1-3}$ alkylene) optionally hydroxy substituted preferably oligo- or polyglycerol ethers such as those described in GB-A-1,539,625, for example containing up to 10 glycerol units; and wherein $R^1$ is joined via an amide linkage to an amino acid unit of the polyaminoacid. It is to be understood herein that the term acyl includes alkenoyl and alkynoyl groups as well as alkanoyl groups.

The hydrophobic group may be selected from hydrophobic drugs or ligands, steroid derivatives, hydrophobic macrocyclics or organic chains.

Preferred hydrophobic organic chains include $C_{12-24}$ alkyl, alkanoyl, alkenyl, alkenoyl, alkynyl or alkynoyl straight or branched chains.

The compound has a degree of substitution by the hydrophilic groups in the range (hydrophilic groups:amino acid monomers) of 1:40–1:1, preferably 1:20–1:2. The compound has a degree of substitution by the hydrophobic groups in the range (hydrophobic groups:amino acid monomers) of 1:20–1:1, preferably 1:10–1:2.

The ratio of substituent hydrophilic:hydrophobic groups in the compounds of this invention is in the range 20:1 to 1:20, preferably 10:1 to 1:10, for example 5:1.

A preferred range of compounds are substituted poly-L-lysines or poly-L-ornithines wherein a free amine of a lysine or ornithine monomer is substituted with mono- or oligo-hydroxy $C_{1-6}$ alkyl, mono- or oligo-hydroxy substituted $C_{2-6}$ acyl, $C_{1-2}$ alkoxy alkyl optionally having one or more hydroxy groups substituted on the alkoxy or alkylene groups, oligo- or poly-(oxa $C_{1-3}$ alkylene) such as polyoxy-ethylene comprising up to about 120 ethylene oxide units and $C_{1-4}$ alkyl (oligo- or poly-oxa $C_{1-3}$ alkylene) optionally hydroxy substituted such as polyglycerol ethers, for example containing up to 10 glycerol units; and a free amine of a further lysine or ornithine is substituted with $C_{12-24}$ alkyl, alkanoyl, -alkenyl, alkenoyl-alkynyl or alkynoyl.

Particularly preferred compounds are palmitoyl poly-L-lysine polyethylene glycol (PLP) (see FIG. 1) or palmitoyl poly-L-ornithine polyethylene glycol (POP).

The compounds may be formed by first reacting a polyamino acid with the hydrophilic group followed by reaction with the hydrophobic group.

The compounds described herein are used in combination with cholesterol or a derivative thereof to form vesicles. In the absence or cholesterol, particle formation does not occur and the material precipitates. Consequently, the presence of cholesterol is required to promote self-assembly of the polyamino acids to form vesicles.

The vesicles are made by techniques similar to those used to form liposomes and niosomes, for instance by blending the compounds in an organic solvent and then contacting the dried mixture with an aqueous solution, optionally followed by a particle size reduction step. Alternatively vesicles may be prepared by sonicating a mixture of modified polymers and cholesterol in the presence of an aqueous solvent.

The vesicles formed may be suspended in an aqueous vehicle or alternatively may be freeze-dried. The vesicles may optionally incorporate a steric stabilizer, for instance a non-ionic amphiphilic compound, preferably a poly-24-oxyethylene cholesteryl ether. The vesicles may be in the micron or nanometer size range, nanometer sized vesicles being formed preferably in the presence of the steric stabilizer. In this case, the steric stabilizer is incorporated into the structure of the vesicle.

The vesicles preferably also comprise an associated pharmaceutically active ingredient. The active ingredient may be water soluble, in which case it will be associated with the hydrophilic regions of the particle, or water insoluble and consequently associated with the hydrophobic regions of the particle.

Such an ingredient is preferably physically entrapped within the particle but may also be held by covalent conjugation. The pharmaceutically active ingredient may be a peptide or protein therapeutic compound. A further preferred alternative for the pharmaceutically active compound is nucleic acid (e.g. DNA), preferably in the form of a gene for gene therapy or gene vaccination.

These pharmaceutical carrying vesicles may be used for the treatment of a human or animal by therapy, in particular for oral drug delivery of peptides or proteins or as gene delivery vectors. It is envisaged that this drug delivery system will also be useful when used via the intravenous, intramuscular, intraperitonial or topical (inhalation, intranasal, application to the skin) routes.

Other agents may be included in a pharmaceutical formulation comprising the vesicles of the present invention. Such other agents may include agents which improve the pharmacology of the vesicles such as chloroquine and primary, secondary or tertiary amines.

The pharmaceutical composition may optionally further comprise a pharmacologically acceptable carrier.

BRIEF DESCRIPTION OF THE DRAWINGS

The present invention will now be further described by way of reference to the following non-limiting examples and the Figures, in which.

EXAMPLE 1

Figure 1:
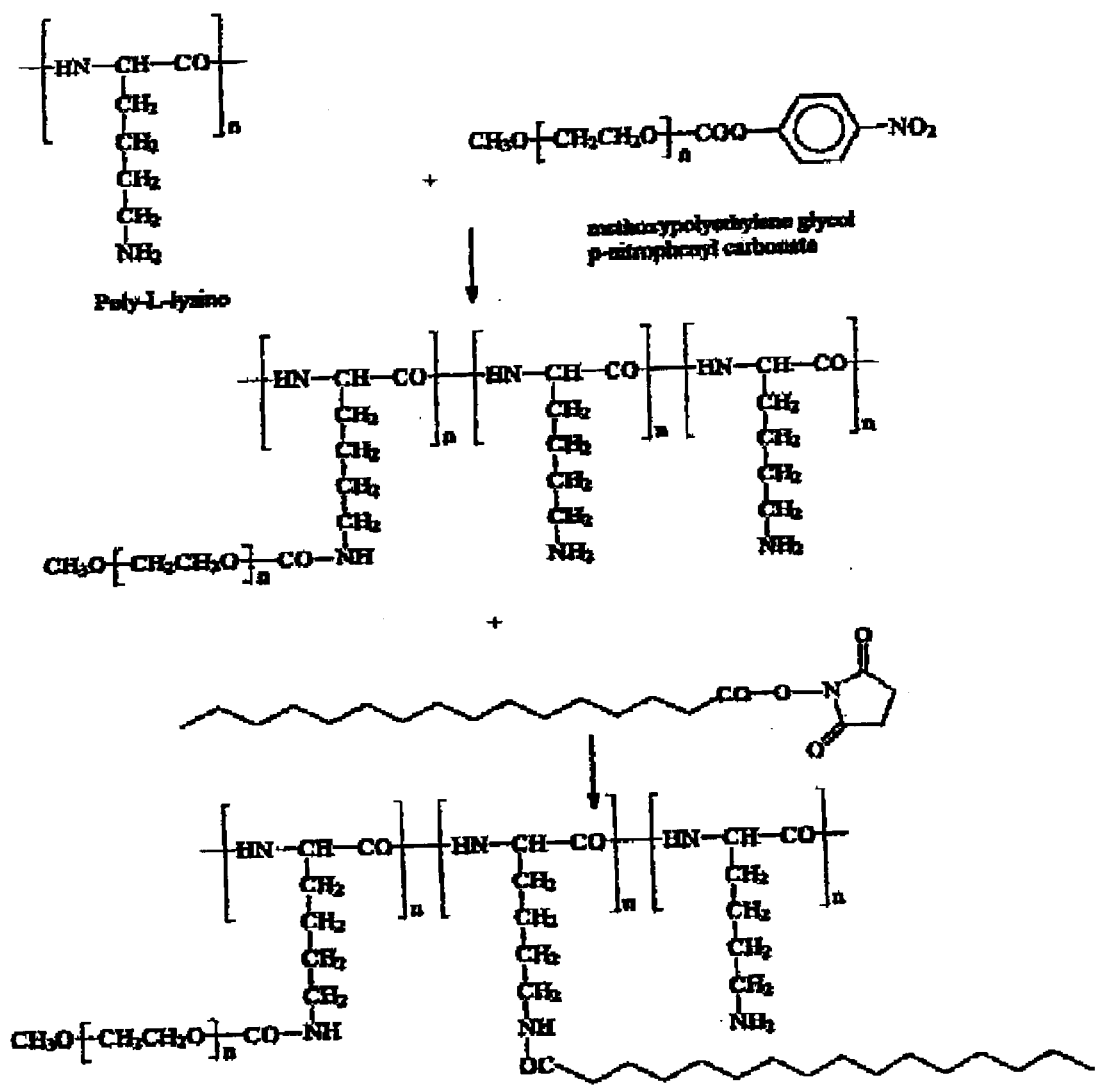
FIG. 1 shows schematically the synthesis of PLP.

The modified polymers were synthesised according to the scheme shown in FIG. 1.

Preparation of PLP

Poly-L-lysine (100 mg) was dissolved in 0.08M sodium tetraborate. (60 mL). Over a 3 h period and with stirring methoxypolyethyleneglycol p-nitrophenyl carbonate (Mw~5,000,180 mg) was added in three portions. This reaction mixture was stirred overnight protected from light. The following morning the reaction mixture was dialysed against water (5 L) with six changes over a 24 h period. Sodium hydrogen carbonate (250 mg) was then dissolved in the dialysed liquid and palmitic acid N-hydroxysuccinimide (60 mg) dissolved in absolute ethanol (76 mL) added dropwise to the dialysed liquid over a 1 h period with stirring. The reaction mixture was stirred for 72 h protected from light and subsequently dialysed against 5 L of water with six changes over a 24 h period. The dialysed material was freeze dried for three days and the freeze-dried solid dissolved in 100 mL of chloroform. The chloroform solution was filtered and the filtrate evaporated under reduced pressure at 30–40° C. until the volume had been reduced to about 5 mL. This solution was added dropwise to 50 mL of diethyl ether and the precipitate collected by filtration. To obtain a dry powder the precipitate was freeze-dried further.

Preparation of POP

Poly-L-ornithine (100 mg) was dissolved in 0.08M sodium tetraborate. (60 mL). Over a 3 h period and with stirring methoxypolyethyleneglycol p-nitrophenyl carbonate (MW~5,000,200 mg) was added in three portions. This reaction mixture was stirred overnight protected from light. The following morning the reaction mixture was dialysed against water (5 L) with six changes over a 24 h period. Sodium hydrogen carbonate (250 mg) was then dissolved in the dialysed liquid and palmitic acid N-hydroxysuccinimide (65 mg) dissolved in absolute ethanol (80 mL) added dropwise to the dialysed liquid over a 1 h period with stirring. The reaction mixture was stirred for 72 h protected from light and subsequently dialysed against 5 L of water with six changes over a 24 h period. The dialysed material was freeze dried for three days and the freeze-dried solid dissolved in 100 mL of chloroform. The chloroform solution was filtered and the filtrate evaporated under reduced pressure at 30–40° C. until the volume has been reduced to about 5 mL. This solution was added dropwise to 50 mL of diethyl ether and the precipitate collected by filtration. To obtain a dry powder the precipitate was freeze-dried further.

EXAMPLE 2

Preparation of Drug Loaded PLP and POP Vesicles

PLP (5 mg) and cholesterol (2 mg) was dispersed in a 2 mL solution of doxorubicin HCl (1 mg mL$^{-1}$) in PBS (pH=4.0). The mixture was sonicated for 2×2 min with the instrument (Soniprobe, Lucas Dawe Ultrasonics) set at 20% of its maximum output. The dispersion was filtered (0.45 μm) and centrifuged (150,000 g×1 h, MSE 75 suppressed). The supernatant was separated from the pellet and the pelleted vesicles disrupted by 10× the volume of isopropanol. Both the vesicle and supernatant fraction were analysed fluorimetrically according to the technique described in Uchegbu et al (1994) Biopharm Drug Dispos 15: 691–707 (ex. 480 nm, exc. 560 nm).

POP (10 mg) and cholesterol (4 mg) were dispersed in a 2 mL solution of doxorubicin HCl (1 mg mL$^{-1}$) in PBS (pH=4.0). The mixture was sonicated for 2×2 min with the instrument set at 20% of its maximum output. The dispersion was filtered (0.45 μm) and centrifuged (150,000 g×1 h, MSE 75 suppressed). The supernatant was separated from the pellet and the pelleted vesicles disrupted by 10× the volume of isopropanol. Both the vesicle and supernatant fraction were analysed fluorimetrically (ex. 480 nm, exc. 560 nm).

Table 1 shows that PLP and POP are able to encapsulate doxorubicin.

EXAMPLE 3

Preparation of DNA Loaded PLP and POP Vesicles

Plasmids (pEGFPCl) grown in an overnight *E. Coli* culture and purified by ion exchange (Qiagen Maxiprep®) were incubated with different amounts of PLP-cholesterol (10:4) or POP-cholesterol (3:2) vesicles. The ratio of PLP and POP to DNA was varied from 0:1 to 20:1 gg$^{-1}$. At various time intervals an aliquot of the incubation mixture containing 10 μg of plasmid in 0.1 mL was added to 3.8 mL of ethidium bromide (40 μg mL$^{-1}$) and the fluorescence read (excitation=526 nm, emission=592 nm). The fluorescence of uncondensed plasmid was obtained by adding 10 μg of plasmid in 0.1 mL to 3.8 mL of ethidium bromide (40 μg mL$^{-1}$) and measuring the flurescence (excitation=526 nm, emission=592 nm).

Figure 2:
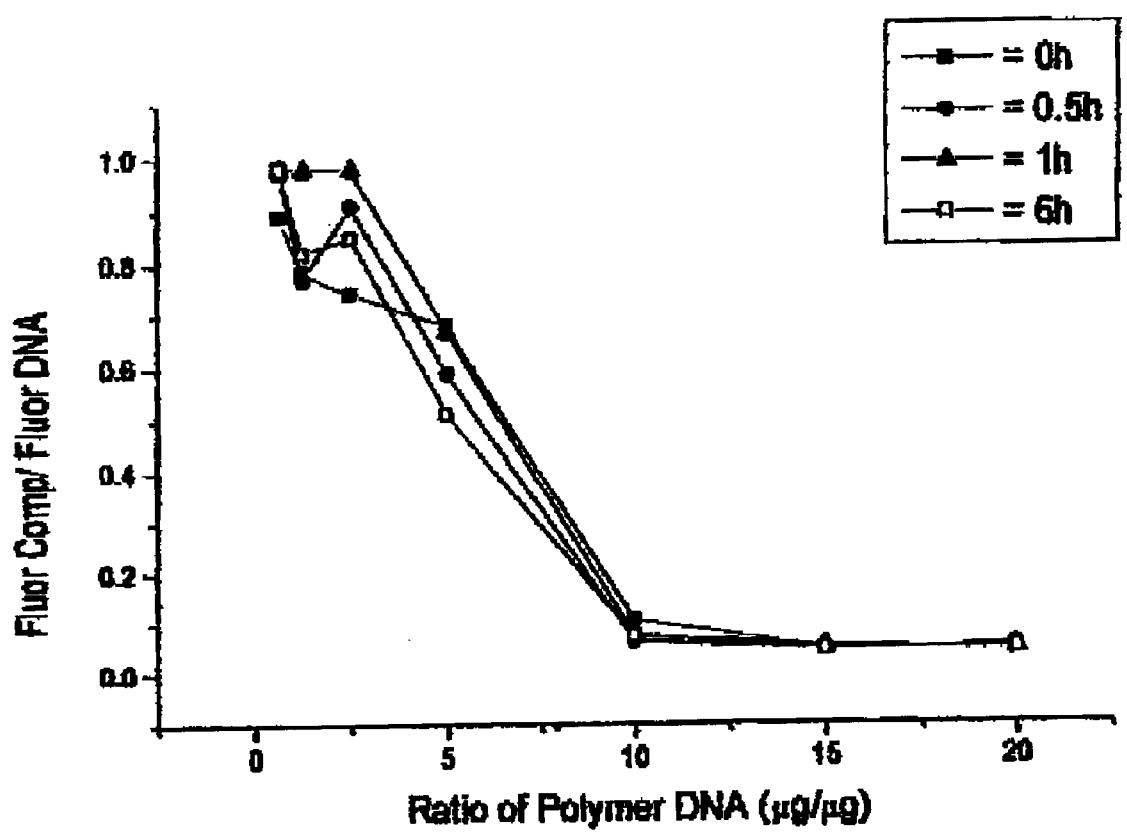
FIG. 2 shows ethidium bromide exclusion (as shown by a decrease in fluorescence) on complexation of DNA with POP-cholesterol vesicles (pH=4), wherein fluorescence of naked DNA and ethidium bromide is given a value of 1. Fluor. Comp=fluorescence of the polymeric vesicle–DNA complex+ethidium bromide, fluor DNA=fluorescence of naked DNA+ethidium bromide.
Figure 3:
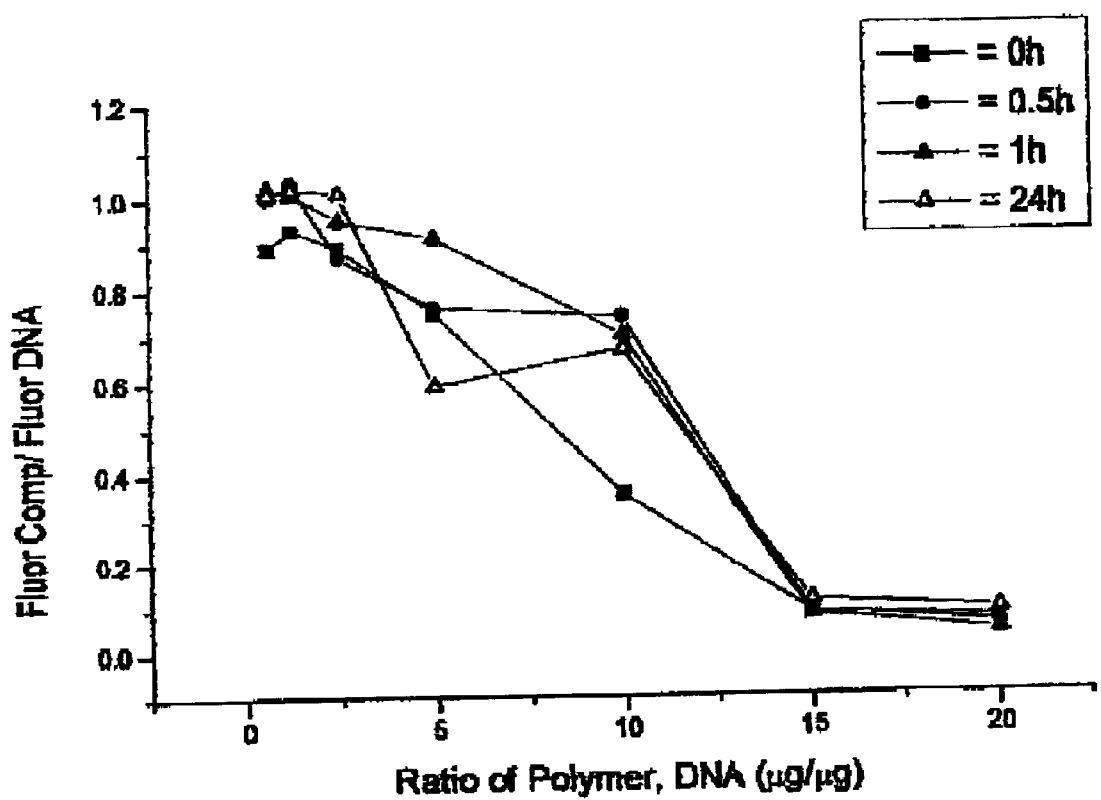
FIG. 3 shows the results of ethidium bromide exclusion on complexion of PLP-cholesterol vesicles (pH=4) in the manner according to FIG. 2.

PLP and POP vesicles were able to condense DNA and form stable complexes (sea FIGS. 2 and 3) once the ratio of polymer to DNA exceeds 10–15:1 (gg$^{-1}$) DNA polymeric vesicle complexes have been found to be stable for up to 24 hrs and remain in the colloidal size range as a non-sedimenting cloudy liquid was obtained.

PLP based vesicles could also be visualized by freeze-fracture electron microscopy after storage for 9 months at refrigeration temperature.

EXAMPLE 4

Efficacy of DNA Loaded PLP and POP Vesicles

Transfection experiments were carried out with the endotoxin free pCMV-sport-β-gal plasmid. 96-well plates were seeded with A549 calls (10,000 cells well$^{-1}$, 50,000 cells mL$^{-1}$) and incubated overnight with DMEM/F10+10% foetal calf serum (FCS)-Life Sciences, UK in 2% CO$_2$ at 37° C. POP vesicles were prepared as described in example 3 and incubated with varying ratios of a β-galactosidase reporter plasmid (p-CMV-SPORT-β-gal, 7.9 kb) for 1 h. The media was removed from the cells and the POP plasmid complexes added (0.1 mL) followed by the addition of Optimem reduced serum media (0.1 mL)-Life Sciences, UK. The mixture was incubated for 4 h (2% CO$_2$, 37° C.) after which the media and POP-plasmid complexes were removed and replaced with DMEM/F10+10% FCS (0.2 mL). Cells were fed daily (DMEM/F10+10% FCS) over a 48 h period at the end of which they were lysed by the addition of 0.05 mL triton X-100 buffer (0.1% triton X-100, 0.25M tris hydrochloride, pH=8.0). The cells were then frozen at −70° C. and thawed at room temperature and 0.5% bovine serum albumin in phosphate buffered saline (0.05 mL) added to each well. This was followed by the addition of 0.15 mL ONPG (o-nitrophenyl β-D-galactopyranoside) in buffer (0.06M sodium dibasic phosphate, 0.001M magnesium chloride, 0.01M potassium chloride, 0.05M β-mercaptoethanol, pH=8.0). β-galactosidase activity was estimated by measuring the absorbance (420 nm) on a microtitre plate reader.

Figure 4:
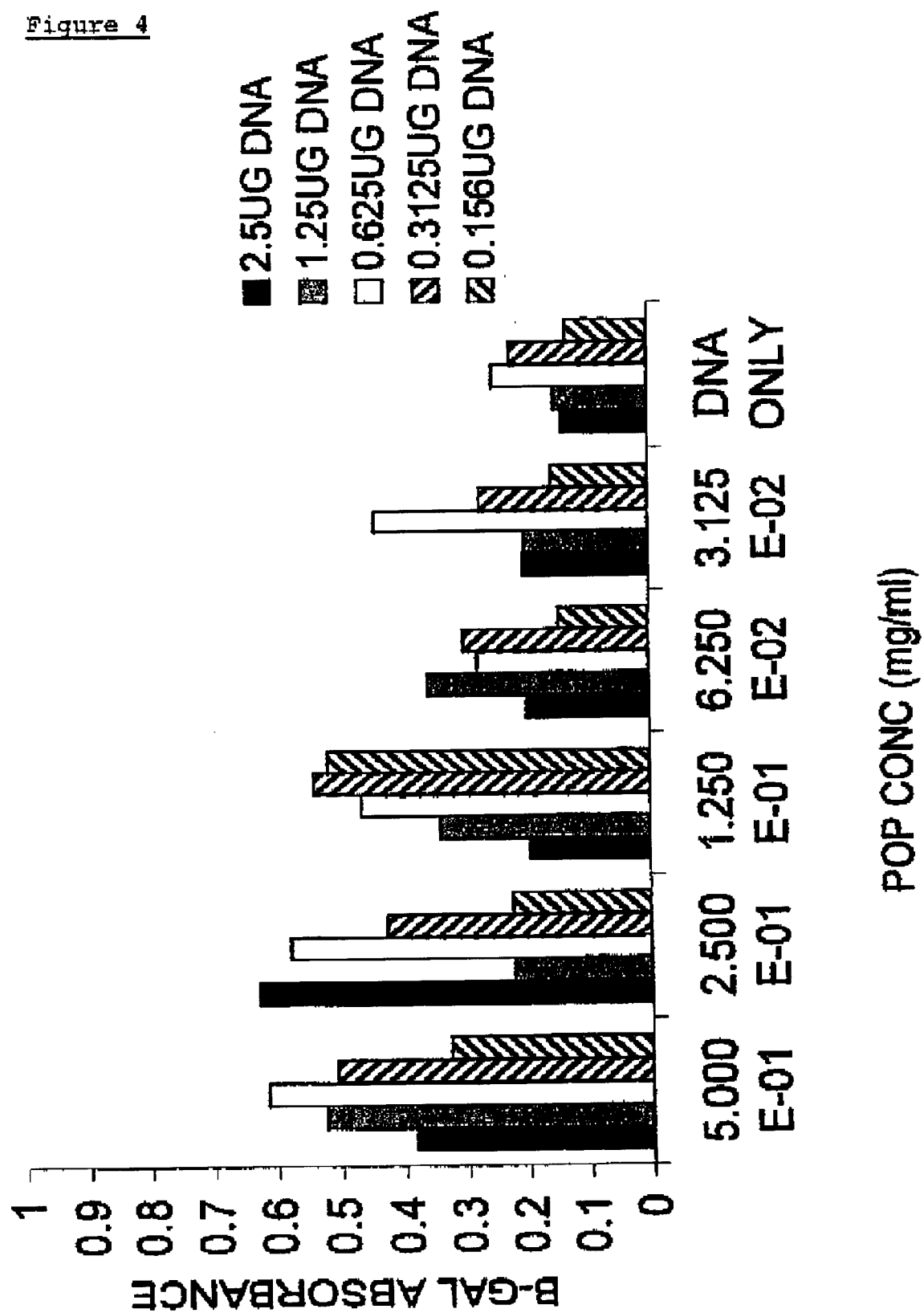
FIG. 4 shows the absorbance levels after transfection of A549 cells with POP: cholesterol vesicles complexed to pCMV-sport-β-gal plasmid+50 μM chloroquine.

The addition of 50 μM chloroquine during transfection was found to increase transfection levels and hence, could be acting to aid removal of the systems from the lysosomes (see FIG. 4).

TABLE 1

Size and encapsulation efficiency of PLP and POP particulate drug carriers.

| Particulate sample | Particle size (nm) | Encapsulation efficiency Doxorubicin, POP/PLP (gg$^{-1}$) |
|---|---|---|
| POP, Cholesterol + doxorubicin | 361 ± 13 | 0.014 ± 0.0042 |
| PLP, cholesterol + doxorubicin | 531 ± 56 | 0.01177 ± 0.0015 |

What is claimed is:

1. A pharmaceutical composition comprising vesicles, said vesicles comprising a derivatised polyamino acid bearing at least one hydrophilic group per molecule, wherein said hydrophilic group is bound to a side group of the polyamino acid molecule, and at least one hydrophobic group per molecule, wherein said hydrophobic group is bound directly to a free amine of a side group of the polyamino acid molecule and wherein said hydrophobic group is other than an alkenoyl; said composition further comprising cholesterol, or a derivative thereof, which promotes vesicle formation; and a pharmaceutically active agent.

2. The pharmaceutical composition according to claim 1 wherein the polyamino acid is a straight chain homopolymer joined by amide linkages.

3. The pharmaceutical composition according to claim 2 wherein the straight chain homopolymer is selected from poly-L-lysine or poly-L-ornithine.

4. The pharmaceutical composition according to claim 1 wherein the polyamino acid is a straight chain heteropolymer joined by amide linkages.

5. The pharmaceutical composition according to claim 1 wherein the polyamino acid has a molecular weight in the range of 600 to 1,000,000.

6. The pharmaceutical composition according to claim 5 wherein the polyamino acid has a molecular weight in the range of 15,000 to 30,000.

7. The pharmaceutical composition according to claim 1 wherein the hydrophilic group is cationic.

8. The pharmaceutical composition according to claim 1 wherein the hydrophilic group is non-ionic.

9. The pharmaceutical composition according to claim 1 wherein the hydrophilic group is selected from hydrophilic drug molecules or ligands, sugars, oligosaccharides, polyhydroxy molecules or organic groups.

10. The pharmaceutical composition according to claim 9 wherein the hydrophilic group is selected from mono- and oligo-hydroxy $C_{1-6}$ alkyl, mono- and oligo-hydroxy substituted $C_{2-6}$ acyl, $C_{1-2}$ alkoxy alkyl optionally having one or more hydroxy groups substituted on the alkoxy or alkylene groups, oligo- or poly-(oxa $C_{1-3}$ alkylene), or $C_{1-4}$ alkyl (oligo- or poly-oxa $C_{1-3}$ alkylene).

11. The pharmaceutical composition according to claim 1 wherein the hydrophobic group is selected fronm hydrophobic drugs or ligands, steroid derivatives, hydrophobic macrocyclics or organic chains.

12. The pharmaceutical composition according to claim 11 wherein the hydrophobic group is selected from $C_{12-24}$ alkyl, alkanyol, alkynyl or alkynoyl straight or branched chains.

13. The pharmaceutical composition according to claim 1 wherein the degree of substitution by the hydrophilic groups is in the range of 1:40 to 1:1 (hydrophilic groups:amino acid monomers).

14. The pharmaceutical composition according to claim 1 wherein the degree of substitution by the hydrophobic groups is in the range of 1:2 to 1:1 (hydrophobic groups:amino acid monomers).

15. The pharmaceutical composition according to claim 1 wherein the ratio of substituted hydrophilic:hydrophobic groups is in the range of 20:1 to 1:20.

16. The pharmaceutical composition according to claim 1 wherein the derivatised poly amino acid is selected from a substituted poly-L-lysine or poly-L-ornithine wherein a free amine or a lysine or ornithine monomer is substituted with a hydrophilic group selected from a mono- or oligo-hydroxy substituted $C_{2-6}$ acyl, a $C_{1-2}$ alkoxyl alkyl optionally having one or more hydroxy groups substituted on the alkoxy or alkylene groups, an oligo- or poly-(oxa $C_{1-3}$ alkylene); and a free amine of a further lysine or ornithine is substituted with a hydrophobic group selected from $C_{12-24}$ alkanoyl, $C_{12-24}$ alkenyl, $C_{12-24}$ alkynyl or $C_{12-24}$ alkynoyl.

17. The pharmaceutical composition according to claim 16 wherein the derivatised poly amino acid is palmitoyl poly-L-lysine polyethylene glycol.

18. The pharmaceutical composition according to claim 16 wherein the derivatised polyamino acid is palmitoyl-poly-L-ornithine polyethylene glycol.

19. The pharmaceutical composition according to claim 1, wherein the pharmaceutically active agent is entrapped in the vesicle.

20. The pharmaceutical composition according to claim 1 wherein the pharmaceutically active agent is covalently conjugated to the vesicle.

21. The pharmaceutical composition according to claim 1 in which the pharmaceutically active agent is selected from the group consisting of a peptide therapeutic, a protein therapeutic compound and DNA.

22. The pharmaceutical composition according to claim 21 wherein the DNA is in the form of a gene for use in gene therapy or gene vaccination.

23. The pharmaceutical composition according to claim 1 for use in a drug delivery system.

* * * * *

UNITED STATES PATENT AND TRADEMARK OFFICE
CERTIFICATE OF CORRECTION

PATENT NO. : 6,576,254 B1
DATED : June 10, 2003
INVENTOR(S) : Uchegbu

It is certified that error appears in the above-identified patent and that said Letters Patent is hereby corrected as shown below:

Column 6,
Table 1, Line 37, "0.01177" should read -- 0.0117 --.

Column 7,
Line 30, "1:2" should read -- 1:20 --.

Column 8,
Line 16, after "palmitoyl" cancel the dash (-).

Signed and Sealed this

Seventh Day of October, 2003

JAMES E. ROGAN
*Director of the United States Patent and Trademark Office*